United States Patent
Lange et al.

(10) Patent No.: US 11,787,773 B2
(45) Date of Patent: Oct. 17, 2023

(54) PROCESS FOR THE PRODUCTION OF FURFURAL

(71) Applicant: SHELL OIL COMPANY, Houston, TX (US)

(72) Inventors: Jean-Paul Andre Marie Joseph Ghislain Lange, Amsterdam (NL); Juben Nemchand Chheda, Houston, TX (US)

(73) Assignee: SHELL USA, INC., Houston, TX (US)

( * ) Notice: Subject to any disclaimer, the term of this patent is extended or adjusted under 35 U.S.C. 154(b) by 199 days.

(21) Appl. No.: 17/605,778

(22) PCT Filed: May 19, 2020

(86) PCT No.: PCT/EP2020/063976
§ 371 (c)(1),
(2) Date: Oct. 22, 2021

(87) PCT Pub. No.: WO2020/234303
PCT Pub. Date: Nov. 26, 2020

(65) Prior Publication Data
US 2022/0227725 A1    Jul. 21, 2022

Related U.S. Application Data

(60) Provisional application No. 62/851,153, filed on May 22, 2019.

(51) Int. Cl.
*C07D 307/48*  (2006.01)
(52) U.S. Cl.
CPC .................................. *C07D 307/48* (2013.01)
(58) Field of Classification Search
CPC .................................................. C07D 307/48
See application file for complete search history.

(56) References Cited

U.S. PATENT DOCUMENTS

| | | | |
|---|---|---|---|
| 2,078,241 A | 4/1937 | Fulmer et al. | |
| 2,536,732 A | 1/1951 | Dunlop | |
| 3,549,319 A | 12/1970 | Wilson et al. | |
| 4,409,032 A | 10/1983 | Paszner et al. | |
| 4,461,648 A | 7/1984 | Foody | |
| 4,533,743 A | 8/1985 | Medeiros et al. | |
| 5,536,325 A | 1/1996 | Brink | |
| 5,789,210 A | 8/1998 | Ho et al. | |
| 5,820,687 A | 10/1998 | Farone et al. | |
| 6,475,768 B1 | 11/2002 | Otero et al. | |
| 7,741,084 B2 | 6/2010 | Viitanen et al. | |
| 7,741,119 B2 | 6/2010 | Viitanen et al. | |
| 7,781,191 B2 | 8/2010 | Dunson, Jr. et al. | |
| 8,168,807 B2 | 5/2012 | Wabnitz et al. | |
| 8,466,242 B2 | 6/2013 | Geremia et al. | |
| 10,899,725 B2 | 1/2021 | Chheda et al. | |
| 2003/0162271 A1 | 8/2003 | Zhang et al. | |
| 2009/0061490 A1 | 3/2009 | Edwards et al. | |
| 2010/0019191 A1 | 1/2010 | Hoffer et al. | |
| 2010/0312028 A1 | 12/2010 | Olson et al. | |
| 2012/0107887 A1 | 5/2012 | Chheda et al. | |
| 2012/0122152 A1 | 5/2012 | Blackbourn et al. | |
| 2012/0157697 A1 | 6/2012 | Burket et al. | |
| 2012/0302765 A1 | 11/2012 | Dumesic et al. | |
| 2013/0295629 A1 | 11/2013 | Weider et al. | |
| 2014/0018555 A1 | 1/2014 | De Vries et al. | |
| 2014/0107355 A1 | 4/2014 | Dumesic et al. | |

FOREIGN PATENT DOCUMENTS

| | | |
|---|---|---|
| EP | 1727890 A1 | 12/2006 |
| EP | 1863901 A1 | 12/2007 |
| RU | 1365674 A1 | 7/1996 |
| SU | 1759825 A1 | 9/1992 |
| WO | 9742307 A1 | 11/1997 |
| WO | 2007009463 A2 | 1/2007 |
| WO | 2007028811 A1 | 3/2007 |
| WO | 2007136762 A2 | 11/2007 |
| WO | 2008119082 A2 | 10/2008 |
| WO | 2009109631 A1 | 9/2009 |
| WO | 2009130386 A1 | 10/2009 |
| WO | 2011161141 A1 | 12/2011 |

(Continued)

OTHER PUBLICATIONS

International Search Report and Written Opinion received for PCT Patent Application No. PCT/EP2020/063976, dated Jul. 27, 2020, 09 pages.
Zeitsch et al., "The Chemistry and Technology of Furfural and its Many By-Products", lst Edition, Sugar Series 13, pp. 48-51 and 303-306.
Lee et al., "Removal of Furan and Phenolic Compounds From Simulated Biomass Hydrolysates by Batch Adsorption and Continuous Fixed-bed Column Adsorption Methods, Biotechnology", vol. 216, 2016, pp. 661-668.
Palkovits, "Selective Liquid Phase Adsorption of 5-Hydroxymethylfurfural on Nanoporous Hyper-Cross-Linked Polymers", ACS Sustainable Chem. Eng, vol. 2, pp. 2407-2415.
International Search Report and Written Opinion received for PCT Patent Application No. PCT/US2017/058936, dated Feb. 7, 2018, 9 pages.

(Continued)

*Primary Examiner* — Golam M Shameem
(74) *Attorney, Agent, or Firm* — SHELL USA, INC.

(57) ABSTRACT

A process for the production of furfural from a biphasic composition including furfural, an organic solvent and soluble organic debris. The said process includes subjecting the biphasic composition to a liquid-liquid separation step to provide an organic phase and an aqueous phase. The organic phase includes the organic solvent, a first portion of the furfural and a first portion of soluble organic debris. The aqueous phase includes a remainder portion of the furfural and a remainder portion of soluble organic debris. The organic phase is subjected to a distillation step to provide a furfural stream and an organic solvent stream including the organic solvent and the first portion of the soluble organic debris. The organic solvent stream is conveyed to an adsorption unit to adsorb a second portion of the soluble organic debris, forming an organic debris-depleted recycle stream.

10 Claims, 6 Drawing Sheets

(56) References Cited

FOREIGN PATENT DOCUMENTS

| WO | 2012027279 A1 | 3/2012 |
|---|---|---|
| WO | 2012041990 A1 | 4/2012 |
| WO | 2014105289 A1 | 7/2014 |
| WO | 2016025678 A1 | 2/2016 |
| WO | 2016025679 A1 | 2/2016 |
| WO | 2018085174 A1 | 5/2018 |
| WO | 2020094526 A1 | 5/2020 |

OTHER PUBLICATIONS

International Search Report and Written Opinion received for PCT Patent Application No. PCT/US2015/044994, dated Nov. 2, 2015, 8 pages.
International Search Report and Written Opinion received for PCT Patent Application No. PCT/US2015/044990, dated Nov. 2, 2015, 7 pages.
International Search Report and Written Opinion received for PCT Patent Application No. PCT/US2017/058942, dated Jan. 19, 2018, 9 pages.
International Search Report and Written Opinion received for PCT Patent Application No. PCT/US2017/058939, dated Dec. 14, 2017, 8 pages.
International Search Report and Written Opinion received for PCT Patent Application No. PCT/US2017/058951, dated Jan. 2, 2018, 8 pages.
Brown et al., "Fast Pyrolysis and Bio-Oil Upgrading", Biomass-lo-Diesel Workshop; Pacific Northwest National laboratory, Sep. 5-6, 2006, 46 pages.
Galbe et al., "A Review of the Production of Ethanol from Softwood", Applied Microbiology and Biotechnology, vol. 59, 2002, pp. 618-628.
Ong, "Conversion of Lignocellulosic Biomass to Fuel Ethanol—A Brief Review", The Planter, vol. 80, Issue No. 941, Aug. 2004, pp. 517-524.
Moller, "Cell Wall Saccharification", Outputs from the EPOBIO Project, Nov. 2006, pp. 1-69.
Mosier et al., "Features of Promising Technologies for Pretreatment of Lignocellulosic Biomass", Bioresource Technology, vol. 96, 2005, pp. 673-686.
Holtzapple et al., "The Ammonia Freeze Explosion (AFEX) process—A Practical Lignocellulose Pretreatment", Applied Biochemistry and Biotechnology, vol. 28/29, Issue No. 1, Mar. 1991, pp. 59-74.
Kumar et al., "Methods for Pretreatment of Lignocellulosic Biomass for Efficient Hydrolysis and Biofuel Production", Industrial & Engineering Chemistry Research, vol. 48, Issue No. 8, 2009, pp. 3713-3729.
Lavarack et al., "The Acid Hydrolysis of Sugarcane Bagasse Hemicellulose to Produce Xylose, Arabinose, Glucose and other Products", Biomass & Bioenergy, vol. 23, Issue No. 5, 2002, pp. 367-380.
Yang et al., "One-Step Catalytic Transformation of Carbohydrates and Cellulosic Biomass to 2, 5 Dimethyltetrahydrofuran for Liquid Fuels", Chem Sus Chem, vol. 3, Issue No. 5, May 25, 2010, pp. 597-603.
Lange et al., "Furfural-A Promising Platform for Lignocellulosic Biofuels", Chem Sus Chem, vol. 5, Issue No. 1, Jan. 9, 2012, pp. 150-166.
Nhien et al., "Design and Optimization of Intensified Biorefinery Process for Furfural Production Through a Systematic Procedure", Biochemical Engineering Journal, vol. 116, Apr. 5, 2016, pp. 166-175, XP029805891.
International Search Report and Written Opinion received for PCT Patent Application No. PCT/US2015/044981, dated Nov. 2, 2015, 8 pages.
Office Action Received for Chinese Application No. 202080036770. 5, dated Apr. 22, 2023, 14 Pages (8 Pages of English Translation and 6 Pages of Official Copy).

PROCESS FOR THE PRODUCTION OF FURFURAL

CROSS-REFERENCE TO RELATED APPLICATION

This is a National stage application of International Application No. PCT/EP2020/063976, filed May 19, 2020 which claims the benefit of U.S. Provisional Application No. 62/851,153, filed May 22, 2019, entitled PROCESS FOR THE PRODUCTION OF FUFURAL, the entirety of which is incorporated by reference herein.

FIELD OF THE INVENTION

The present invention relates to a process for the extraction of furfural from a biphasic dehydration reaction mixture in a resource and energy efficient manner by the use of one or more adsorption units to enrich the furfural content of an organic solvent stream to remove soluble organic debris from an organic solvent stream used to extract furfural from a biphasic dehydration reaction mixture.

BACKGROUND OF THE INVENTION

Furfural is a useful precursor for industrial chemicals such as in producing furan and its derivatives.

Furfural may be produced from xylose which in turn is produced from the hydrolysis of feedstock including lignocellulosic biomass. Lignocellulosic biomass includes mainly cellulose, hemicelluloses and lignin, and smaller amounts of protein. Hemicelluloses are a branched polysaccharide of heterogeneous monosaccharide content whose molecular structure includes the five-carbon monosaccharides (otherwise generically referred to as "pentoses") such as xylose and arabinose, as well as the six-carbon monosaccharides (otherwise generically referred to as "hexoses") such as glucose, mannose, galactose and rhamnose. Due to their xylose and arabinose content, hemicelluloses are a suitable source of monomeric and polymeric pentoses. In comparison, cellulose is a linear-polysaccharide made up of polymerised glucose (a six-carbon monosaccharide/hexose). Compared to cellulose, hemicelluloses are easier to breakdown into their constituent monosaccharides.

A commercially available feedstock comprising lignocellulosic biomass includes bagasse which is the fibrous matter that remains after sugarcane or sorghum stalks are crushed and their juices are extracted. In some embodiments, the lignocellulosic biomass is selected from the group including, but not limited to, corn stover, straw, bagasse, miscanthus, sorghum residue, switch grass, bamboo, water hyacinth, hardwood, hardwood, softwood, wood chips, and wood pulp.

An established continuous process for the production of furfural from bagasse is the Rosenlew process, the details of which are discussed in "The Chemistry and Technology of Furfural and its Many By-Products", 1st Edition, K. Zeitsch, pages 48-51 and 303-306. However, other processes for the production of furfural also exist.

For example, WO2012041990 describes the production of furfural from bagasse-derived hemicellulose, via its gaseous acid catalysed hydrolysis to pentoses, which are then dehydrated to produce furfural.

For example, WO2016025678 describes the production of furfural, where initially hemicellulose is hydrolysed in a solution comprising α-hydroxysulfonic acid, a portion of the α-hydroxysulfonic acid is then removed from the hydrolysis reaction product to produce an acid-removed stream, and finally the acid-removed stream is subjected to a dehydrating step to produce furfural.

For example, WO2016025679 describes a hydrolysis step, which is buffered to less than pH 1, followed by a dehydrating step to produce furfural.

In both WO2016025678 and WO2016025679, during the dehydration reaction step, a "biphasic" dehydration reaction mixture is formed by the addition of "a water-immiscible organic phase" (i.e. a solvent) into the dehydration reaction mixture. The solvent extracts a portion of the furfural produced in the biphasic dehydration reaction mixture. The biphasic dehydration reaction mixture is then separated into an aqueous product stream and an organic product stream comprising a portion of furfural. However, WO2016025678 and WO2016025679 do not disclose how furfural can be fully recovered and purified from the organic product stream comprising furfural. Further, it is not clear from the disclosures in WO2016025678 and WO2016025679 how the efficiency of furfural recovery from the dehydration reaction mixture can be improved.

Lee S. C. & Park S. (2016) have disclosed in Biotechnology 216, pages 661-668, that powdered activated charcoal may be used to remove contaminants such as furans from simulated biomass hydrolysates. The example of a furan provided is furfural. However, Lee & Park does not discuss furfural recovery from the biphasic dehydration reaction mixtures/compositions comprising organic solvent(s) and does not disclose how to selectively desorb furfural from the powdered activated charcoal.

Palkovits (2014) has disclosed in ACS Sustainable Chem. Eng. 2, pages 2407-2415, that hyper-branched carbon polymers made by crosslinking alkylation of dichloro-biphenyl have a very high surface area, pore volume and hydrophobicity, and will adsorb hydroxymethylfurfural with high selectivity and with a high uptake. However, Palkovits does not discuss furfural recovery from the biphasic dehydration reaction mixtures/compositions comprising organic solvent(s) and does not disclose how to selectively desorb the furfural from the hyper-branched carbon polymer.

It would, therefore, be advantageous to provide a process to manage soluble organic debris in the organic solvent to minimize the furfural yield loss in the biphasic reaction. The soluble organic debris can build up to levels in the organic recycle loop causing furfural yield loss and solid by-product formation, both of which are undesirable.

SUMMARY OF THE INVENTION

Accordingly, the present invention provides a process for the production of furfural from a biphasic composition comprising furfural, organic solvent and soluble organic debris. The process includes subjecting the biphasic composition to a liquid-liquid separation step to provide an organic phase (organic solvent, a first portion of the furfural and a first portion of soluble organic debris) and an aqueous phase (remainder portion of the furfural and a remainder portion of soluble organic debris). The organic phase is subjected to a distillation step to provide a furfural stream and an organic solvent stream (the organic solvent and the first portion of the soluble organic debris). The organic solvent stream is conveyed to an adsorption unit to adsorb a second portion of the soluble organic debris, and to form an organic debris-depleted recycle stream.

DETAILED DESCRIPTION OF THE INVENTION

Figure 1:
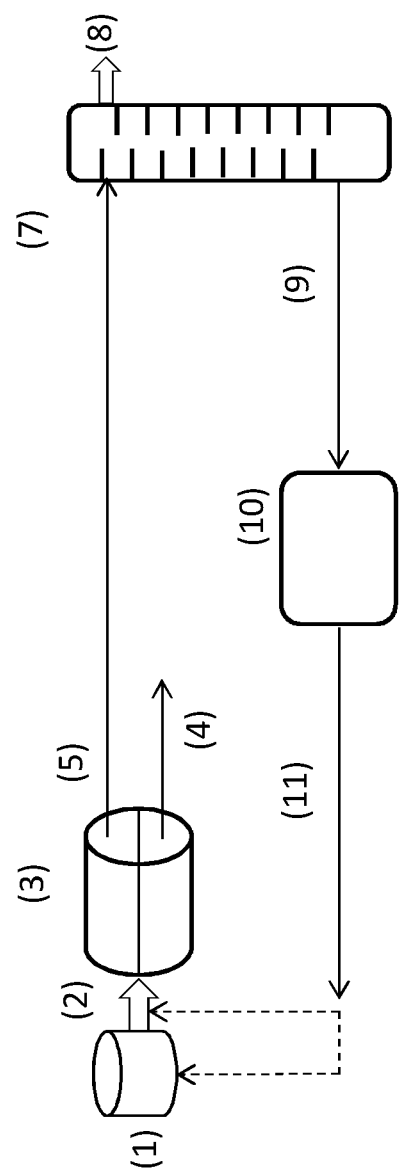
FIG. 1 shows a simplified schematic diagram of an embodiment of the process according to the invention with a solvent having a boiling point higher than furfural.

The following description of the variations is merely illustrative in nature and is in no way intended to limit the scope of the disclosure, its application, or uses. The description and examples are presented herein solely for the purpose of illustrating the various embodiments of the disclosure and should not be construed as a limitation to the scope and applicability of the disclosure.

The terminology and phraseology used herein is for descriptive purposes and should not be construed as limiting in scope. Language such as "including," "comprising," "having," "containing," or "involving," and variations thereof, is intended to be broad and encompass the subject matter listed thereafter, equivalents, and additional subject matter not recited.

Also, as used herein any references to "one embodiment" or "an embodiment" means that a particular element, feature, structure, or characteristic described in connection with the embodiment is included in at least one embodiment. The appearances of the phrase "in one embodiment" in various places in the specification are not necessarily referring to the same embodiment.

The present inventors have found that the process for the extraction of furfural according to the present invention provides a higher yield of furfural than known processes, consumes less energy to produce each tonne of furfural, and consumes less material, in particular, less organic solvent, suitably, by the removal of soluble organic debris from a solvent stream, for example from the furfural-depleted solvent stream (i.e. after furfural is distilled from the solvent stream, to provide solvent recycle stream that is depleted of soluble organic debris) and/or for example from a furfural-containing solvent stream (i.e. prior to the further extraction of the furfural, to provide an organic debris depleted solvent stream for e.g. furfural distillation).

In the process according to the present invention, furfural is extracted from the "biphasic" dehydration reaction mixture referred to in WO2016025678 and WO2016025679. The biphasic dehydration reaction mixture comprises an aqueous phase and an organic phase comprising furfural and an organic solvent.

The biphasic dehydration reaction mixture can be derived from a pentose dehydration step wherein monomeric and polymeric pentoses are dehydrated at an elevated temperature.

In turn, the monomeric and polymeric pentoses used for said dehydration step may be produced by hydrolysing lignocellulosic biomass in the presence of at least one acid, as described in WO2016025678 and WO2016025679. The acid catalyst used in the dehydration step ("dehydration acid") can be an organic or an inorganic acid (other than α-hydroxysulfonic acids) as long as it can catalyze the dehydration of C5 carbohydrates to furfural and/or its derivatives. Preferred inorganic acid, may include mineral acids, for example, such as HCl, HNO3, H2SO4, H3PO4, and the like. Organic acids may include, for example, acetic acid, formic acid, oxalic acid, levulinic acid, toluene sulfonic acid, citric acid, etc.

Preferably, the pentose dehydration step is carried out at elevated temperatures of at least 100° C., more preferably at least 110° C., and even more preferably at least 140° C. Preferably, the pentose dehydration step is carried out at elevated temperatures of at most 250° C., more preferably at most 200° C., and even more preferably at most 150° C.

Preferably, the pentose dehydration step is carried out for a period of at least 1 second, more preferably at least 5 minutes, even more preferably at least 10 minutes and most preferably at least 30 minutes. Preferably, the pentose dehydration step is carried out for a period of at most 24 hours, more preferably at most 12 hours, even more preferably at most 5 hours and most preferably at most 2 hours.

The biphasic dehydration reaction mixture comprises furfural, water, an organic solvent, soluble organic debris and aqueous components. The organic solvent may have a boiling point higher than the boiling point of furfural or lower than the boiling point of furfural. In a preferred embodiment, the organic solvent has a boiling point higher than the boiling point of furfural. The organic solvent may be an aromatic solvent, a phenolic solvent, or mixtures thereof.

Due to the immiscibility of the organic solvent with the aqueous components of the dehydration reaction mixture, the organic solvent's presence in the dehydration reaction mixture leads to the formation of the biphasic dehydration reaction mixture. If this mixture is allowed to settle, the organic solvent will separate from the aqueous phase of the dehydration reaction mixture to form an organic phase that is distinct from the aqueous phase.

Suitably, furfural formed in the aqueous phase has a preference to partition into the organic solvent rather than remain in the aqueous phase. The partitioning of furfural into the organic solvent forms the organic phase. The extent of furfural's partitioning into the organic phase from the aqueous phase depends on, amongst other things, the partition coefficient of furfural across the interface between water and a given organic solvent. For example, in the presence of equal parts by weight of water and an aromatic solvent, about 80% of the furfural will partition into the aromatic solvent, while the remaining about 20% will remain in the aqueous phase. The partition coefficient may also depend on temperature.

However, a proportion of soluble organic debris also partitions into the organic phase. The presence of soluble organic debris in the organic phase is unwanted, as it can build up in the hardware and lead to fouling. Fouling can cause the inefficient operation of such hardware, due to blockages and faults that lead to increased hardware downtime. Fouling also can lead to furfural yield loss. Further, the presence of soluble organic debris in the organic phase can render the organic solvent unusable, and therefore unavailable for recycling back into the biphasic dehydration reaction, thus increasing running costs.

Faced with these problems, the inventors have surprisingly found that, in particular, at least one adsorption unit can be used to recover soluble organic debris from the organic phase, for example, after a distillation step that recovers furfural from the organic phase.

In some embodiments, the soluble organic debris in the organic phase may also be removed by the use of at least one adsorption unit present, for example, after a liquid-liquid separation step, but before the organic phase is fed into subsequent downstream steps, such as a distillation step used to extract furfural from the organic phase.

Such adsorption units enable the recycling of a cleaner organic solvent stream, for example, back into the dehydration reaction, or back into the liquid-liquid separation step that takes place after the dehydration reaction step.

In one embodiment, the organic solvent may be added to the aqueous dehydration reaction mixture at the start of the pentose dehydration step, or part way through it.

In other embodiments, the organic solvent may also be added after the completion of the pentose dehydration step, to the aqueous dehydration product stream, such as if the pentose dehydration step did not occur in the presence of the organic solvent.

In some embodiments, the source of the organic solvent added to the dehydration reaction mixture may be from a fresh source of the organic solvent or may be from a stream recycled from one or more steps downstream of the biphasic dehydration reaction. The organic solvent may also be a mixture in varying proportions of both fresh and recycled organic solvent.

If the organic solvent is added to the biphasic dehydration reaction mixture at the start of, or part way through the pentose dehydration step, simultaneous with its production, furfural will partition predominantly into the organic phase. The level of furfural partitioning into the organic phase will continue to the extent possible in accordance with the relevant partitioning coefficient.

Adding the organic solvent to the biphasic dehydration reaction mixture at the start of, or part way through the pentose dehydration step, enables the simultaneous extraction of furfural from the dehydration reaction mixture, thus protecting furfural from degradation by removing it from the dehydration reaction mixture.

In some embodiments, the aqueous phase to total organic solvent phase has a ratio of at least 1:0.05 by volume, more preferably said ratio is at least 1:0.1 by volume, even more preferably said ratio is at least 1:0.25 by volume, most preferably said ratio is at least 1:0.4 by volume.

In some embodiments, the aqueous phase to total organic solvent ratio is at most 1:2.5 volume, more preferably said ratio is at most 1:1.25 volume, even more preferably said ratio is at most 1:0.75 volume, most preferably said ratio is at most 1:0.6 volume.

In some embodiments, a mixture of organic solvents may include organic solvents having a boiling point higher than furfural and organic solvents having a boiling point lower than furfural. In a preferred embodiment, a mixture of organic solvents, each with a boiling point higher than that of furfural, may be used.

In some embodiments, the aromatic solvent is selected from compounds such as, but not limited to, 1-ethyl-2,3-dimethylbenzene, 1-ethyl-2,5-dimethylbenzene, 1-ethyl-2,4-dimethylbenzene, 1-ethyl-3,4-dimethylbenzene, 1,2,3,5-tetramethylbenzene, 1,2,3,4-tetramethylbenzene, 1,2,4,5-tetramethylbenzene, naphthalene, 1-methylnaphthalene, 2-methylnaphthalene, n- and sec-propyl-methyl benzenes (with the methyl group located in 2-, 3-, 4- or 5-position) n- and sec-butyl benzene and n- and sec-pentyl benzene. The aromatic solvent may also be selected from compounds such as, but not limited to, dimethyl naphthalene, ethyl naphthalene, diethyl naphthalene, methyl ethyl naphthalene, propyl naphthalene, butyl naphthalene, pentyl naphthalene, hexyl naphthalene, methyl propyl naphthalene, methyl butyl naphthalene, methyl pentyl naphthalene, methyl hexyl naphthalene. Suitable alkylated naphthalenes can also include, for example, AROMATIC® 200 fluid, AROMATIC® 200 ND fluid, AROMATIC® 150 fluid, or AROMATIC® 150 ND fluid, all available from ExxonMobil. Suitable alkylated naphthalenes also include AROMATIC® 100 fluid available from Shell Oil Company. The aromatic solvent may also be selected from compounds such as toluene, benzene, m-, p-, o-xylenes, cymene, and cumene.

In some embodiments, the aromatic solvent has a ratio of aromatic carbons to aliphatic carbons of greater than 1. If the aromatic solvent is a pure compound, the ratio of aromatic carbons to aliphatic carbons will be evident to the skilled person. However, if the aromatic solvent is a mixture of one or more of such compounds, a method of determining the ratio of aromatic carbons to aliphatic carbons may be by subjecting the aromatic solvent mixture to $^{13}C$ NMR analysis and obtaining a ratio of the peaks representing the aromatic and aliphatic moieties by techniques known in the art. In some embodiments, the aromatic solvent is selected from benzene, alkyl benzene compounds of 7 or more carbons, naphthalene, and alkyl naphthalene compounds of 11 or more carbons.

In some embodiments, the phenolic solvent may be selected from the group consisting of, but not limited to, propyl guaiacol, propyl syringol, guaiacyl propanol, syringyl propanol, nonyl phenol, o-, m-, p-substituted cresols, guaiacol, 2-methoxy-4-propylphenol, eugenol, sec-butyl phenol, 2,6-xylenol, 2,5-xylenol, tert-butyl phenol, pentyl phenol, hexyl phenol, and dodecyl phenol.

In one embodiment, the phenolics solvent may be sec-butyl phenol or tert-butyl phenol.

In another embodiment, the organic solvent is a mixture of aromatic and phenolic solvents, in particular, a mixture of alkylated naphthalene and alkylated phenolic solvents.

In embodiments of the invention, the organic phase includes the organic solvent, a portion of the furfural, heavy soluble by-products and soluble organic debris and the aqueous phase comprises a remainder portion of the furfural, the aqueous dehydration reaction mixture, heavy soluble by-products and the other reactants of the dehydration reaction mixture, such as water and organic acids. The aqueous phase may also comprise a small fraction of the organic solvent.

To increase the overall yield of furfural production, the organic phase may be cleaned up to remove the soluble organic debris which can build up in the hardware and lead to fouling. Fouling can cause the inefficient operation of such hardware, due to blockages and faults that lead to increased hardware down-time.

In some embodiments, an adsorption unit can be used to adsorb soluble organic debris from the organic phase. Such adsorption unit, therefore, can be deployed in the process to limit fouling and furfural yield loss by removing the soluble organic debris from the organic phase.

At some point, if the operation of the adsorption unit becomes impaired by the saturation of the adsorption unit with soluble organic debris, the adsorption unit can be taken off-line and the soluble organic debris removed from the unit. To remove the soluble organic debris, the temperature may be raised to "burn" the soluble organic debris off the adsorbent or a solvent may be used to "wash" the soluble organic debris from the adsorbent or some other process, known by one skilled in the art, to remove the soluble organic debris from the absorbent may be used. In some embodiments, multiple adsorption units may be used to such that when one unit is taken off-line for cleaning, another unit may be used to make the process continuous.

In some embodiments, the absorption unit may be place upstream or downstream of the distillation unit which distils the furfural from the organic phase.

FIG. 1 shows a simplified schematic process line up diagram of an embodiment of a process according to the present invention, illustrating the supply of a biphasic dehydration reaction mixture (2) from the dehydration reactor (1) to a liquid-liquid separator (3), wherein the latter phase separates to provide an aqueous phase (4) and an organic phase (5).

The organic phase (5) includes a portion of the furfural, the organic solvent and soluble organic debris. The aqueous phase (4) comprises a remainder portion of the furfural. In some embodiments, the aqueous phase (4) may be sent for further processing to recover any furfural therein while recycling the furfural depleted aqueous phase to the biphasic or pre-treatment step.

Preferably, the liquid-liquid separator (3) may be operated at a temperature of at most 200° C., more preferably at a temperature of at most 180° C., even more preferably at a temperature of at most 160° C., even more preferably at a temperature of at most 140° C., so long as the liquid separates into two phases at the separation temperature.

Preferably, the liquid-liquid separator (3) may be operated at a temperature of at least ambient temperature, more preferably at a temperature of at least 20° C., even more preferably at a temperature of at least 60° C., even more preferably at a temperature of at least 90° C., and most preferably at a temperature of at least 100° C., so long as the liquid separates into two phases at the separation temperature.

The liquid-liquid separation step is carried out in any suitable liquid-liquid separator as would be known to the person skilled in the art.

Prior to entering the liquid-liquid separation step, optionally the biphasic dehydration reaction mixture (2) may be routed through a solid/liquid separation step to remove any insoluble organic debris that may have been formed during the dehydration step, and which may otherwise negatively interfere with the separation of the organic phase from the aqueous phase, or a later separation or purification steps.

The organic phase (5) exits the liquid-liquid separator (3) and is conveyed to a distillation column (7) to distil the furfural from the organic phase stream as a furfural stream (8). The distillation of the organic phase (5) also produces an organic solvent stream (9) comprising the organic solvent and soluble organic debris. The distillation column (7) may be an atmospheric distillation column or a vacuum distillation column or any known separation unit, as would be known to the person skilled in the art.

FIG. 1 depicts an embodiment having the organic solvent with a boiling point higher than furfural. The furfural stream (8) exits the distillation column as a top stream and the organic solvent stream (9) exits as a bottom stream.

Following distillation, the organic solvent stream (9) is conveyed from the distillation column (7) via a line to an adsorption unit (10). As the organic solvent stream (9) flows through the adsorption unit (10), a quantity of the soluble organic debris from the organic solvent stream (9) is adsorbed and retained by the adsorption unit (10), resulting in the production of an organic debris-depleted stream (11) that exits the adsorption unit (10). The organic-debris depleted stream (11) may be recycled to the biphasic reactor (1) or to the liquid-liquid separator (3).

As the soluble organic debris begins to build up in the adsorption unit (10), it may be necessary to clean the adsorption unit (10). In some embodiments, the cleaning of the adsorption unit may include stopping the flow of the organic solvent stream (9) and burning or washing the soluble organic debris from the adsorption unit. The adsorption unit (10) may be cleaned by any known cleaning process, as would be known to the person skilled in the art.

When to stop the flow of the organic solvent stream (9) and start the cleaning of the adsorption unit (10) may be determined by one of ordinary skill in the art. In some embodiments, an unacceptable level of soluble organic debris may be detected in the organic debris-depleted stream (11), prompting a cleaning operation to commence.

Preferably, the adsorption may be carried out at a temperature of at least 30° C., more preferably at a temperature of at least 40° C., and most preferably at a temperature of at least 50° C.

Preferably, the adsorption may be carried out at a temperature of at most 120° C., more preferably at a temperature of at most 100° C., and most preferably at a temperature of at most 70° C.

The adsorption unit (10) contains a solid adsorbent. In some embodiments, the solid adsorbent has a high surface area and/or high pore volume. In some embodiments, the solid adsorbent may be a zeolite. The solid adsorbent may be a metal oxide (such as a zirconia, a silica or a titania) or a mixed oxide (such as aluminosilicates). The metal oxide may be micro-, meso-, or mega-porous. In some embodiments, the solid adsorbent may also comprise polymers or polymeric resins. In other embodiments, the solid adsorbent may also comprise carbon, such as in the form of soot, carbon black, activated carbon, carbon nanotubes, hyper branched polymeric, graphene or graphitic carbon.

Activated carbon is a form of carbon processed to have high surface area or microporosity. For example, one gram of activated carbon may have a surface area in excess of 500 $m^2$.

Activated carbon may be produced from materials of biological origin such as peat, wood, nutshells, coconut husk or coir, as well as from mineralised matter such as coal and lignite. Such materials are subjected to either 'physical' reactivation, and/or to 'chemical' reactivation, both as known in the art.

The 'activation' of the carbon is a result of either exposure to an oxidising atmosphere (during physical reactivation,) or to an acid, strong base or a salt followed by carbonisation (during chemical reactivation).

Whichever way active carbon is produced, the high microporosity makes activated carbon an excellent candidate for its use as an adsorption medium, as its ability to adsorb, bind or interact with other compounds is enhanced by its activated high surface area.

Carbon black on the other hand is produced by the incomplete combustion or thermal decomposition of gaseous or liquid hydrocarbons. It typically has a lower surface area than active carbon.

Depending of the production method, the solid adsorbent comprising carbon in the adsorption unit (10) may have hydrophilic or hydrophobic surface properties.

Suitably, the activated carbon, the carbon black, graphite, the carbon nanotubes or the carbon nanofibers that may be used as the carbon absorbent can be sourced from commercial suppliers known to the skilled person.

In some embodiments, the carbon may be in the form of powder. The fineness of the powder may vary, and the fineness may be chosen according to how a given powder in a given adsorption unit affects the flow pressure across the adsorption unit. Carbon in the form of larger grains or pellets may be chosen if the resistance to flow through the adsorption unit is to be reduced.

The adsorption unit (10) may be fixed-bed or a suspended bed. In the suspended bed case, the suspended bed may contain a liquid-solid disengagement zone based on hydrocyclone, settler, membrane or any other option known to persons skilled in the art.

Figure 2:
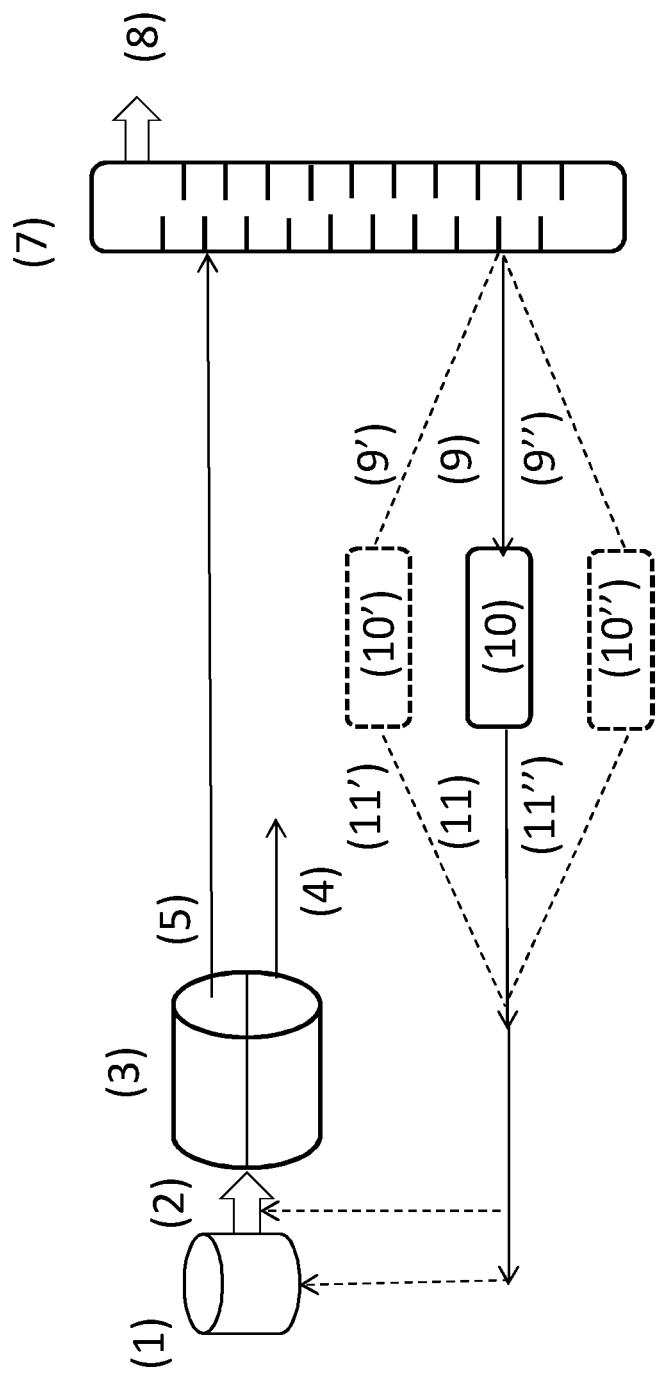
FIG. 2 shows a simplified schematic diagram of another embodiment of the process according to the invention with a solvent having a boiling point higher than furfural and multiple adsorption units.

FIG. 2 shows a simplified schematic process line up of an alternate embodiment of a process according to the present invention, wherein the assigned reference numerals refer to the same steps/streams as in FIG. 1. FIG. 2 additionally depicts more than one adsorption unit (10', 10"), wherein both adsorption units (10', 10") may have an organic debris-depleted stream (11', 11") exiting it.

In this embodiment shown in FIG. 2, as an alternative to the batch-type operation of starting and stopping supply of the organic solvent stream (9) to the adsorption unit (10), the organic solvent stream (9) may be continuously supplied to multiple adsorption units (10, 10', 10" etc.), each working in parallel with the other(s), thus providing continuous operation.

In such embodiments the flow of the organic solvent stream (9) is directed to, and continuously supplied to, a different adsorption unit, whereupon the remaining adsorption units may be undergoing cleaning.

Deploying more than one adsorption unit provides advantages that at least, firstly, the process can be operated continuously thereby increasing the throughput, and at least, secondly, pairs of adsorption units can be taken out of use and serviced without shutting down the process of the present invention.

Other than having more than one adsorption unit, all other aspects of the process and the process line-up of the embodiment in FIG. 2 are the same as in the embodiment of FIG. 1.

Figure 3:
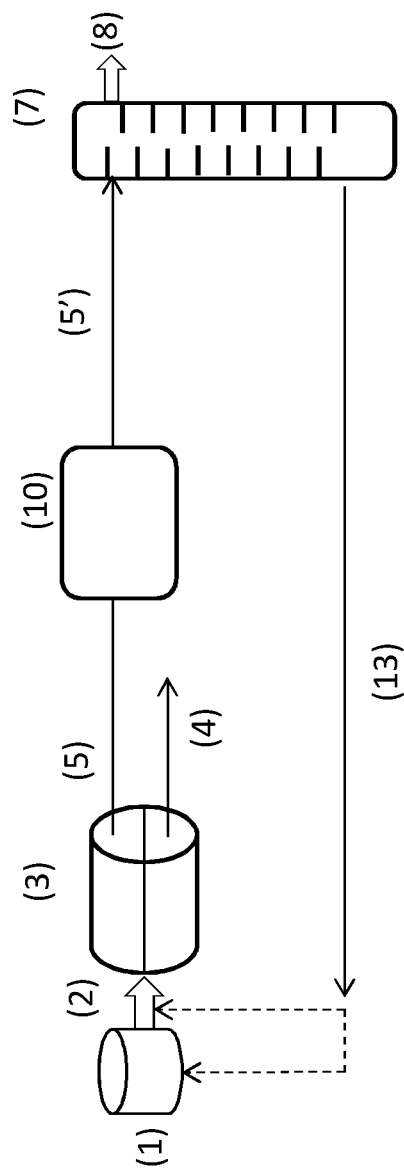
FIG. 3 shows a simplified alternate schematic diagram of an embodiment of the process according to the invention with a solvent having a boiling point higher than furfural and an adsorption unit upstream of a distillation column.

FIG. 3 shows a simplified schematic process line up diagram of an embodiment of a process according to the present invention, illustrating the supply of a biphasic dehydration reaction mixture (2) from the dehydration reactor (1) to a liquid-liquid separator (3), wherein the latter phase separates to provide an aqueous phase (4) and an organic phase (5) which is conveyed to an adsorption unit (10). As the organic phase (5) flows through the adsorption unit (10), a quantity of the soluble organic debris from the organic phase (5) is adsorbed and retained by the adsorption unit (10), resulting in the production of an organic debris-depleted stream (5') that exits the adsorption unit (10).

The organic debris-depleted stream (5') exits the adsorption unit (10) and is conveyed to a distillation column (7) to distil the furfural from the organic debris-depleted stream as a furfural stream (8). The distillation of the organic debris-depleted stream (5') also produces an organic solvent stream (13) comprising the organic solvent.

FIG. 3 depicts an embodiment having the organic solvent with a boiling point higher than furfural. The furfural stream (8) exits the distillation column as a top stream and the organic solvent stream (13) exits as a bottom stream. The organic solvent stream (13) may be recycled to the biphasic reactor (1) or to the liquid-liquid separator (3). Reference numbers remain the same throughout the figures for items identical or similar between the Figures.

Figure 4:
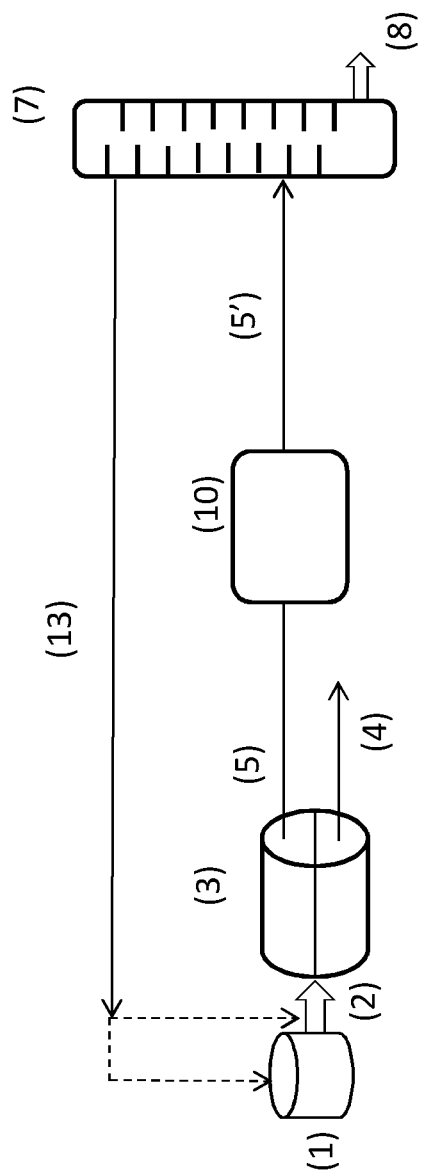
FIG. 4 shows a simplified alternate schematic diagram of an embodiment of the process according to the invention with a solvent having a boiling point lower than furfural and an adsorption unit upstream of a distillation column.

FIG. 4 depicts an embodiment having the organic solvent with a boiling point lower than furfural. The furfural stream (8) exits the distillation column as a bottom stream and the organic solvent stream (13) exits as a top stream. The organic solvent stream (13) may be recycled to the biphasic reactor (1) or to the liquid-liquid separator (3).

Figure 5:
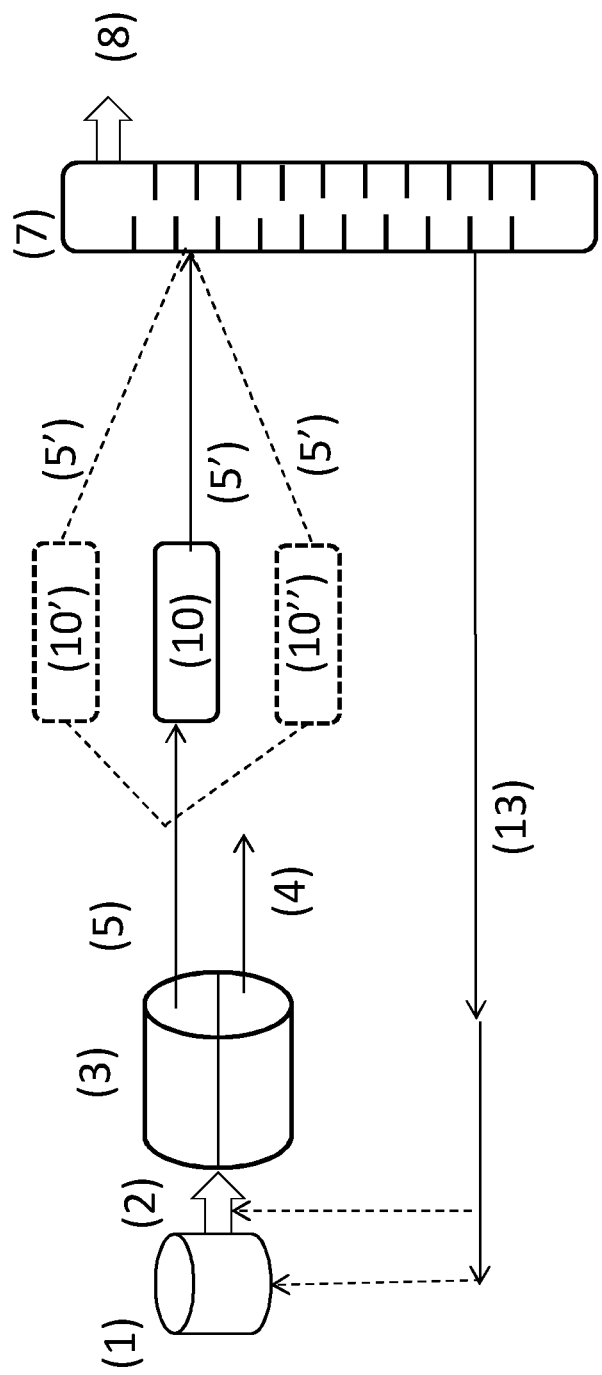
FIG. 5 shows a simplified alternate schematic diagram of another embodiment of the process according to the invention with a solvent having a boiling point higher than furfural and multiple adsorption units upstream of a distillation column.
Figure 6:
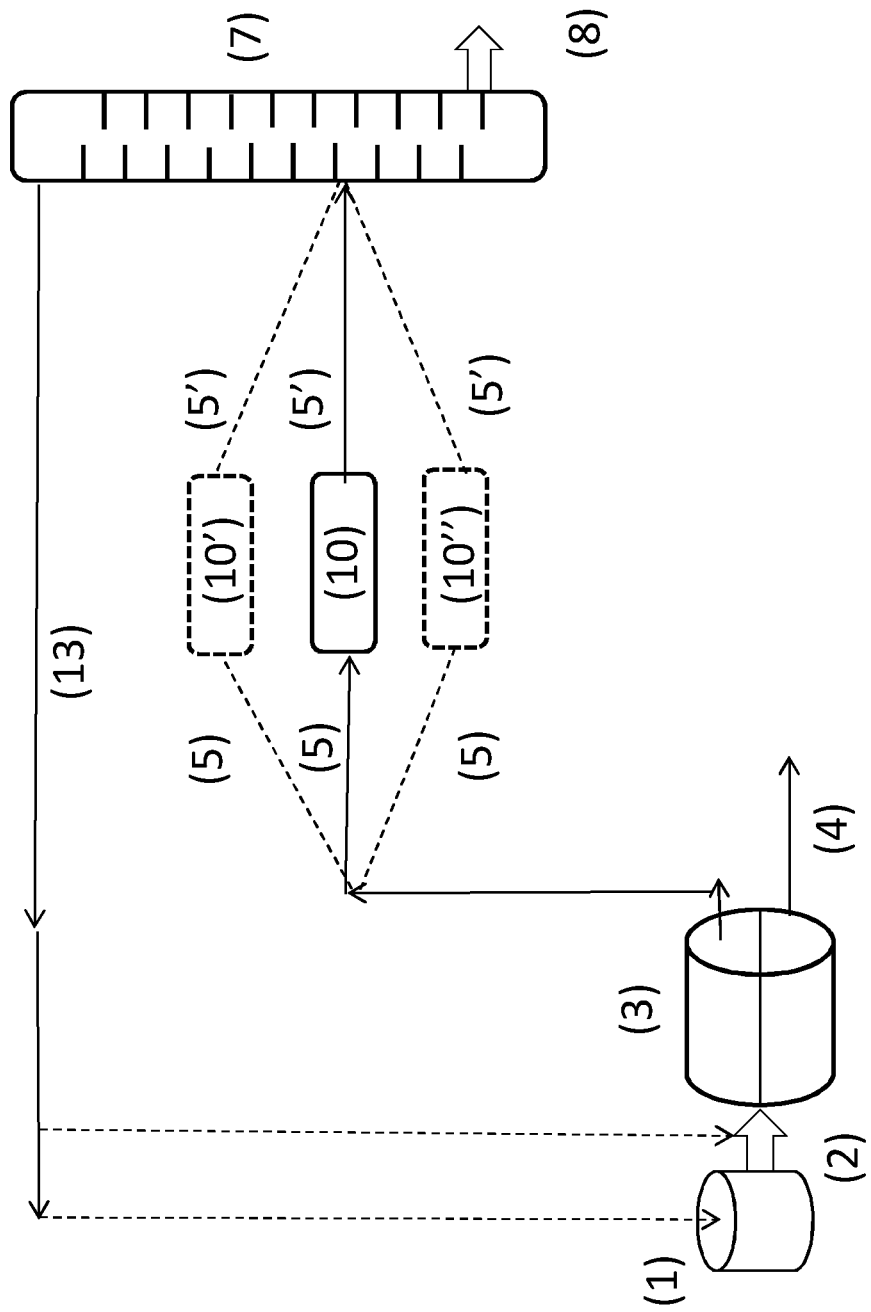
FIG. 6 shows a simplified alternate schematic diagram of another embodiment of the process according to the invention with a solvent having a boiling point lower than furfural and multiple adsorption units upstream of a distillation column.

FIGS. 5 and 6 show simplified schematic process line up diagrams of alternate embodiments of a process according to the present invention, wherein the assigned reference numerals refer to the same steps/streams as in FIGS. 3 and 4. FIGS. 5 and 6 additionally depict more than one adsorption unit (10', 10"), wherein both adsorption units (10', 10") may have an organic debris-depleted stream (5') exiting it.

In these embodiments shown in FIGS. 5 and 6, as an alternative to the batch-type operation of starting and stopping supply of the organic phase (5) to the adsorption unit (10), the organic phase (5) may be continuously supplied to multiple adsorption units (10, 10', 10" etc.), each working in parallel with the other(s), thus providing continuous operation.

In such embodiments, the flow of the organic phase (5) are directed to, and continuously supplied to, a different adsorption unit, whereupon the remaining adsorption units may be undergoing cleaning.

Deploying more than one adsorption unit provides advantages that at least, firstly, the process can be operated continuously thereby increasing the throughput, and at least, secondly, pairs of adsorption units can be taken out of use and serviced without shutting down the process of the present invention.

Other than having more than one adsorption unit, all other aspects of the process and the process line-up of the embodiments in FIGS. 5 and 6 are the same as in the embodiments of FIGS. 3 and 4, respectively.

The present invention is further illustrated in the following Examples.

Example 1

Biphasic dehydration was conducted in a batch reactor (500 ml Zipperclave) at 170° C. and 1 h of residence time with an aqueous feed stream (280 gm). Toluene (140 gm) was used as the organic solvent in the ratio of 1:0.5 by weight relative to the aqueous feed. The aqueous layer was quantified using an HPLC Bio-RAD 87H column and refractive index detector (Bio-Rad, CA), while furfural in the organic phase was quantified using a GC FID analysis using DB-1301 capillary column (Agilent, CA).

After separation in a separatory funnel, the composition of the streams of both the aqueous and organic phase were as presented in Table 1, for both before and after reaction. Overall, about a 62% furfural yield was obtained.

As known by one skilled in the art, the soluble organic debris in the organic phase was further analyzed with a Gel Permeation Chromatography (GPC) column and using a UV detector at 280 nm. The fraction of heavies is quantified as the area fraction under the GPC trace above 162 Daltons. Polystyrene standards were used for calibration of Molecular weight scale.

The soluble organic debris present in the organic phase amounted to about 3.04% area of the organic phase and consisted of components with molecular weight between 162 and ~500 Dalton. The weight and number-average molecular weight (Mw and Mn) amounted to 294 and 239 Dalton, respectively.

Next, about 10 gm of organic phase was taken in a vial and about 1 gm of Activated Charcoal Norit® (Norit CA1, from wood, chemically activated, powder from Sigma-Aldrich) was added to the vial and mixed vigorously. The vial was then allowed to stand for 24 h. After 24 h, a sample was taken and analyzed using GPC technique. As seen from Table 2, the % Area decrease from 3.04 to 0.89, which means about 70% reduction in the amounts of heavies from the organic phase using activated carbon as adsorbent bed.

TABLE 1

Composition of feed and product

| Aqueous Feed | Before Dehydration (wt %) | After Dehydration (wt %) | |
|---|---|---|---|
| | | Aqueous Phase | Organic Phase |
| Xylose | 6.77 | 0.19 | |
| Glucose | 1.54 | 0.38 | |
| Arabinose | 0.68 | 0 | |
| Formic acid | 0.12 | 0.36 | |
| Acetic acid | 1.6 | 1.62 | |
| Levulinic Acid | 0 | 0.55 | |
| Hydroxymethyl furfural | 0.05 | | |
| Furfural | 0.41 | 0.83 | 3.38 |
| Sulphuric acid | 1 | 1 | |
| Organic Feed | | | |
| Toluene | 100 | | |

TABLE 2

GPC analysis for heavy soluble organic debris.

| | Mn | Mw | % Area |
|---|---|---|---|
| Before Carbon Adsorption | 239 | 294 | 3.04 |
| After Carbon Adsorption | 223 | 259 | 0.89 |

Applicants theorize that by utilizing an adsorption unit which can adsorb soluble organic debris from an organic solvent, while recycling the organic solvent, prevention of furfural yield loss due to the presence of reactive soluble organic debris.

Although a few embodiments of the disclosure have been described in detail above, those of ordinary skill in the art will readily appreciate that many modifications are possible without materially departing from the teachings of this disclosure. Accordingly, such modifications are intended to be included within the scope of this disclosure as defined in the claims.

We claim:

1. A process for the production of furfural from a biphasic composition (2) comprising furfural, an organic solvent and soluble organic debris, said process comprising:
   (a) subjecting the biphasic composition to a liquid-liquid separation step (3) to provide:
       an organic phase (5) comprising the organic solvent, a first portion of the furfural and a first portion of soluble organic debris; and
       an aqueous phase (4) comprising a remainder portion of the furfural and a remainder portion of soluble organic debris;
   (b) subjecting the organic phase (5) to a distillation step (7) to provide:
       a furfural stream (8), and
       an organic solvent stream (9) comprising the organic solvent and the first portion of the soluble organic debris;
   (c) conveying the organic solvent stream (9) comprising the organic solvent to an adsorption unit (10) to adsorb a second portion of the soluble organic debris, and to form an organic debris-depleted recycle stream (11).

2. The process according to claim 1, wherein step (c) is carried out using more than one adsorption unit.

3. The process according to claim 1, wherein the organic solvent has a boiling point higher than furfural.

4. The process according to claim 1, wherein following step (c), the adsorption unit (10) undergoes a soluble organic debris removal step to remove any residual soluble organic debris in the adsorption unit.

5. The process of claim 1, wherein the stream (11) comprising the organic debris-depleted recycle stream is recycled to a biphasic dehydration reactor.

6. A process for the extraction of furfural from a biphasic composition (2) comprising furfural, an organic solvent and soluble organic debris, said process comprising:
   (a) subjecting the biphasic composition to a liquid-liquid separation step (3) to provide:
       an organic phase (5) comprising the organic solvent, a first portion of the furfural and a first portion of soluble organic debris; and
       an aqueous phase (4) comprising a remainder portion of the furfural and a remainder portion of soluble organic debris;
   (b) conveying the organic phase (5) comprising the organic solvent, a first portion of the furfural and a first portion of soluble organic debris to an adsorption unit (10) to adsorb a second portion of the soluble organic debris, and to form an organic debris-depleted stream (5') comprising the organic solvent and the first portion of the furfural;
   (c) subjecting the organic debris-depleted stream (5') comprising the organic solvent and the first portion of the furfural to a distillation step (7) to provide:
       a furfural stream (8), and
       an organic solvent stream (9) comprising the organic solvent.

7. The process according to claim 6, wherein step (b) is carried out using more than one adsorption unit.

8. The process according to claim 6, wherein the organic solvent has a boiling point higher than furfural.

9. The process according to claim 6, wherein following step (b), the adsorption unit (10) undergoes a soluble organic debris removal step to remove any residual soluble organic debris in the adsorption unit.

10. The process of claim 6, wherein the organic solvent stream (9) is recycled to a biphasic dehydration reactor.

* * * * *